US012653468B2

(12) United States Patent
Chen et al.

(10) Patent No.: US 12,653,468 B2
(45) Date of Patent: Jun. 16, 2026

(54) CT IMAGING SYSTEM AND CT DETECTION DEVICE

(71) Applicants: Tsinghua University, Beijing (CN); Nuctech Company Limited, Beijing (CN)

(72) Inventors: Zhiqiang Chen, Beijing (CN); Li Zhang, Beijing (CN); Liang Li, Beijing (CN); Mingzhi Hong, Beijing (CN); Zinan Wang, Beijing (CN); Yongjie Xia, Beijing (CN); Ming Chang, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 0 days.

(21) Appl. No.: 18/832,490

(22) PCT Filed: Dec. 25, 2023

(86) PCT No.: PCT/CN2023/141541
§ 371 (c)(1),
(2) Date: Jul. 23, 2024

(87) PCT Pub. No.: WO2024/140565
PCT Pub. Date: Jul. 4, 2024

(65) Prior Publication Data
US 2025/0099045 A1      Mar. 27, 2025

(30) Foreign Application Priority Data

Dec. 28, 2022    (CN) .......................... 202211698118.7

(51) Int. Cl.
*A61B 6/03*        (2006.01)
*A61B 6/10*        (2006.01)

(52) U.S. Cl.
CPC .............. *A61B 6/032* (2013.01); *A61B 6/107* (2013.01)

(58) Field of Classification Search
CPC ................................ A61B 6/032; A61B 6/107
See application file for complete search history.

(56) References Cited

U.S. PATENT DOCUMENTS 3,434,684 A    3/1969  Query
10,575,796 B2  3/2020  Nayak et al.
(Continued)

FOREIGN PATENT DOCUMENTS

CN        103284741 A    9/2013
CN        203662782 U    6/2014
(Continued)

OTHER PUBLICATIONS

"Chinese Application No. 202211698118.7, First Office Action dated Dec. 15, 2023", (Dec. 15, 2023), 21 pgs.
(Continued)

*Primary Examiner* — Uzma Alam
*Assistant Examiner* — Fani Polyzos Boosalis
(74) *Attorney, Agent, or Firm* — Schwegman Lundberg & Woessner, P.A.

(57) ABSTRACT

The present disclosure provides a CT imaging system and a CT detection device. The CT imaging system includes: a connecting plate, a strong supporting frame, a weak supporting frame, an emitter, a detector, an electrical component and a shielding box. The connecting plate is annular and has a rotating axis. The strong supporting frame is connected to the connecting plate on a side of the connecting plate and includes a first strong supporting frame and a second strong supporting frame distributed at an interval in a circumferential direction of the connecting plate. The weak supporting frame is connected to the connecting plate on a same side of
(Continued)

the connecting plate as the strong supporting frame. The emitter is connected to the first strong supporting frame. The detector is connected to the second strong supporting frame. The electrical component is connected to the weak supporting frame. The shielding box is connected to at least one weak supporting frame.

10 Claims, 3 Drawing Sheets

(56) References Cited

U.S. PATENT DOCUMENTS

| | | | |
|---|---|---|---|
| 10,786,213 | B2 | 9/2020 | Yu |
| 11,039,798 | B2 | 6/2021 | Williams et al. |
| 12,458,303 | B2 * | 11/2025 | Zhang ..................... F16C 37/00 |
| 2018/0110481 | A1 | 4/2018 | Yu |
| 2018/0344263 | A1 | 12/2018 | Nayak et al. |
| 2019/0231281 | A1 | 8/2019 | Williams et al. |
| 2021/0353237 | A1 | 11/2021 | Williams et al. |
| 2023/0301604 | A1 | 9/2023 | Zhang et al. |

FOREIGN PATENT DOCUMENTS

| | | |
|---|---|---|
| CN | 105805172 A | 7/2016 |
| CN | 205643200 U | 10/2016 |
| CN | 107981880 B | 5/2018 |
| CN | 109199425 A | 1/2019 |
| CN | 208492132 U | 2/2019 |
| CN | 210697659 U | 6/2020 |
| CN | 114382786 A | 4/2022 |
| CN | 217827894 U | 11/2022 |
| CN | 109803587 B | 5/2023 |
| CN | 219391867 U | 7/2023 |
| CN | 116763329 A | 9/2023 |
| JP | S5483492 A | 7/1979 |
| JP | 2007037873 A | 2/2007 |
| WO | WO-2010119850 A1 | 10/2010 |
| WO | WO-2024140565 | 7/2024 |

OTHER PUBLICATIONS

"Chinese Application No. 202211698118.7, Second Office Action dated Mar. 9, 2024", (Mar. 9, 2024), 27 pgs.
"International Application No. PCT/CN2023/141541, International Search Report and Written Opinion mailed Mar. 15, 2024", (Mar. 15, 2024), 17 pgs.

* cited by examiner

CT IMAGING SYSTEM AND CT DETECTION DEVICE

CROSS REFERENCE TO RELATED APPLICATION(S)

This application is a U.S. national stage filing under 35 U.S.C. § 371 from International Application No. PCT/CN2023/141541, filed on 25 Dec. 2023, and published as WO2024/140565 on 4 Jul. 2024, which claims the benefit under 35 U.S.C. 119 to Chinese Patent Application No. 202211698118.7, filed on Dec. 28, 2022, the benefit of priority of each of which is claimed herein, and which applications and publication are hereby incorporated herein by reference in their entirety.

TECHNICAL FIELD

The present disclosure relates to a field of radiation detection, and in particular to a CT imaging system and a CT detection device.

BACKGROUND

In CT imaging systems, a supporting framework and a mounting supporting frame are manufactured and assembled separately.

SUMMARY

According to an embodiment of the present disclosure, a CT imaging system is provided, including: a connecting plate being annular and having a rotating axis; a strong supporting frame connected to the connecting plate on a side of the connecting plate, where the strong supporting frame includes a first strong supporting frame and a second strong supporting frame distributed at an interval in a circumferential direction of the connecting plate; a weak supporting frame connected to the connecting plate on a same side of the connecting plate as the strong supporting frame; an emitter connected to the first strong supporting frame; a detector connected to the second strong supporting frame; an electrical component connected to the weak supporting frame; and a shielding box being annular, where an annular shielding cavity with an opening facing the rotating axis is formed inside the shielding box, the shielding cavity is provided with an inlet at the emitter and an outlet at the detector, and the shielding box is connected to at least one weak supporting frame.

In some embodiments, the connecting plate is provided with a plurality of mounting holes, and each of the strong supporting frame and the weak supporting frame is fitted at the mounting hole through a fastener.

In some embodiments, the first strong supporting frame includes: a first flat supporting plate tightly attached to the connecting plate; a first upright plate vertically provided on a side of the first flat supporting plate away from the rotating axis, where the first upright plate is welded on the first flat supporting plate, and the first upright plate is provided with a first opening directly facing the inlet; and two first ear plates located at opposite ends of the first flat supporting plate, where each of the two first ear plates is welded to the first upright plate and the first flat supporting plate; the emitter is connected to the first upright plate, and the emitter is located on a side of the first upright plate away from the shielding box.

Furthermore, the first upright plate is provided with a plurality of connecting threaded holes, and the emitter is fixed at the plurality of connecting threaded holes through a threaded component; and the strong supporting frame further includes a supporting auxiliary plate, and the emitter is located between the supporting auxiliary plate and the first upright plate.

In some embodiments, at least two detectors are arranged at intervals sequentially in the circumferential direction of the connecting plate, each of the at least two detectors is connected to the second strong supporting frame, and the shielding box is provided with the outlet corresponding to each of the at least two detectors.

Furthermore, each second strong supporting frame includes: a second flat supporting plate tightly attached to the connecting plate; a second upright plate vertically provided and welded on the second flat supporting plate; and a second ear plate located on a side of the second upright plate away from the shielding box, where the second ear plate is welded to the second flat supporting plate and the second upright plate; and the detector is connected to the second upright plate.

In some embodiments, the connecting plate is a cast component, the strong supporting frame is a welded or cast component, and the weak supporting frame is a sheet metal component.

In some embodiments, the shielding box is a sheet metal component, the shielding box is provided with a plurality of connecting ears, and the connecting ear is connected to at least one of the weak supporting frame, the electrical component, or the strong supporting frame.

In some specific embodiments, an inner perimeter wall of the shielding box is circular, the connecting plate is toroidal, and the inner perimeter wall of the shielding box is coaxial with the connecting plate; and an inner diameter of the shielding box is less than an inner diameter of the connecting plate.

According to an embodiment of the present disclosure, a CT detection device is provided, including: a supporting framework provided with a bearing mounting hole; a slip ring bearing arranged in the bearing mounting hole; a CT imaging system in above embodiments, where the connecting plate is connected to the slip ring bearing so that the connecting plate is rotatable relative to the supporting framework; and a detection channel mounted on the supporting framework, where the detection channel penetrates the shielding box.

The additional aspects and advantages of the present disclosure will be partially provided in the following description, which will become clear from the following description, or will be learned through the practice of the present disclosure.

BRIEF DESCRIPTION OF THE DRAWINGS

The above and/or additional aspects and advantages of the present disclosure will become clear and easy to be understood from the description of embodiments in conjunction with accompanying drawings, and in the drawings.

DETAILED DESCRIPTION OF EMBODIMENTS

Figure 1:
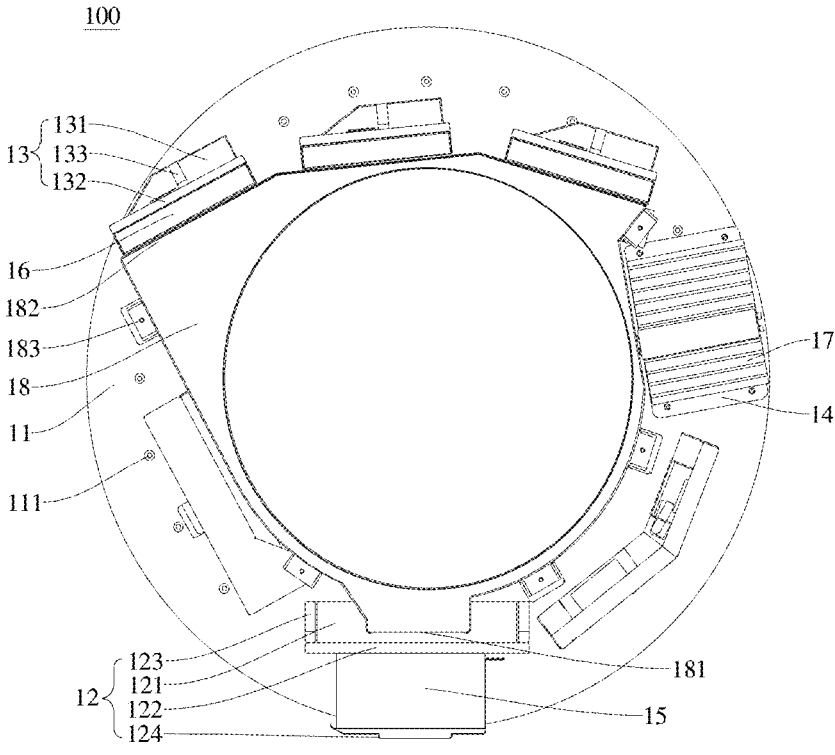
FIG. 1 is a front view of a CT imaging system according to an embodiment of the present disclosure.

Embodiments of the present disclosure are described in detail in the following. Examples of embodiments are shown in the accompanying drawings, where same or similar reference signs throughout represent same or similar components or components with same or similar functions. Embodiments described below with reference to the accompanying drawings are illustrative and intended only to explain the present disclosure, and cannot be understood as a limitation of the present disclosure.

In the description of the present disclosure, it should be understood that the terms "thickness", "up", "inside", "outside", "radial", "circumferential", etc. indicate the orientation or position relationship based on the orientation or position relationship shown in the drawings, only for the convenience of describing and simplifying the description of the present disclosure, rather than indicating or implying that the device or component referred to must have a specific orientation, be constructed and operated in a specific orientation, and therefore cannot be understood as a limitation of the present disclosure. In addition, features defined with "first" and "second" may explicitly or implicitly include one or more of these features. In the description of the present disclosure, unless otherwise specified, "plurality of" means two or more.

In the description of the present disclosure, it should be noted that unless otherwise specified and defined, the terms "mounting", "connection", and "connected" should be broadly understood, for example, it may be fixed connections, detachable connections, or integrated connections; it may be a mechanical connection or an electrical connection; it may be directly connected, or indirectly connected through an intermediate medium, or it may be an internal connection between two components. Those ordinary skilled in the art may understand the specific meanings of the above terms in the present disclosure based on specific circumstances.

In an existing CT imaging system, the assembly process of the supporting framework and the mounting supporting frame is complex. There are many factors that affect a device assembly accuracy, so that a dynamic performance of the supporting framework and the mounting supporting frame is not easy to be ensured, which affects the movement stability and imaging quality of the CT imaging system. In other schemes, a connecting plate and the mounting supporting frame are formed by integral casting, which simplifies the assembly process. However, this scheme is based on high-level casting and composite processing technology. Considering the current accelerated development speed in the industry, the pace of product version iteration is accelerating, resulting in the extremely high cost for the integral casting scheme.

The present disclosure provides a CT imaging system, which may achieve overall lightweight.

In the CT imaging system according to embodiments of the present disclosure, a stable connection between the emitter and the connecting plate as well as a stable connection between the detector and the connecting plate are ensured through the strong supporting frame, thereby ensuring the imaging effect of the CT imaging system, while a connection between the electrical component and the connecting plate as well as a connection between the shielding box and the connecting plate are achieved through the weak supporting frame, thereby reducing the weight of the connection structure and facilitating the overall lightweight of the CT imaging system.

The present disclosure further provides a CT detection device including the above CT imaging system.

In the CT detection device according to embodiments of the present disclosure, by using the CT imaging system in above embodiments, some components in the CT imaging system are connected by using the weak supporting frame, so that the overall lightweight of the CT imaging system may be achieved while ensuring the imaging effect, thereby improving the stability of the CT imaging system when the CT imaging system rotates relative to the supporting framework, and improving the overall stability and detection effect of the CT detection device.

A CT imaging system 100 and a CT detection device 1000 according to embodiments of the present disclosure are described below with reference to the accompanying drawings.

Figure 2:
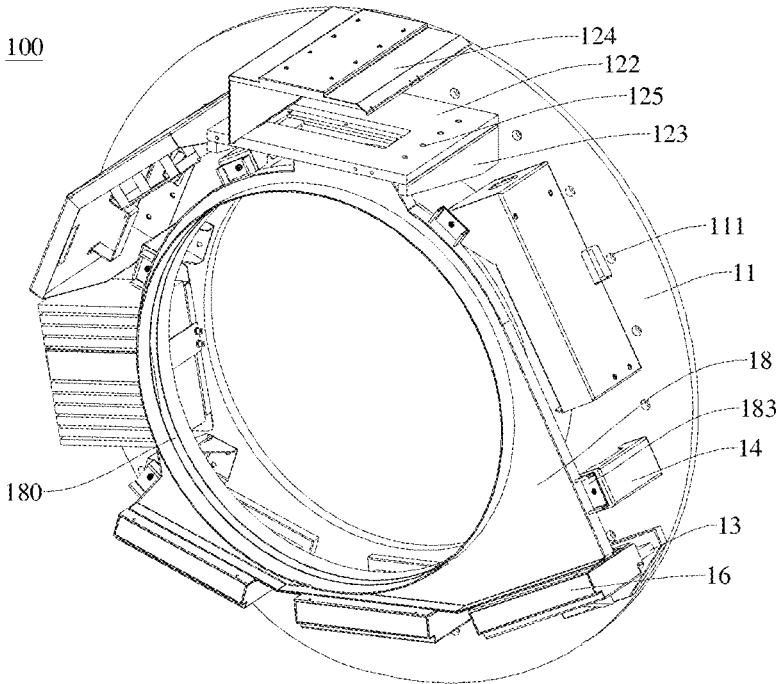
FIG. 2 is a three-dimensional view of the CT imaging system according to the embodiment shown in FIG. 1 in an orientation.
Figure 3:
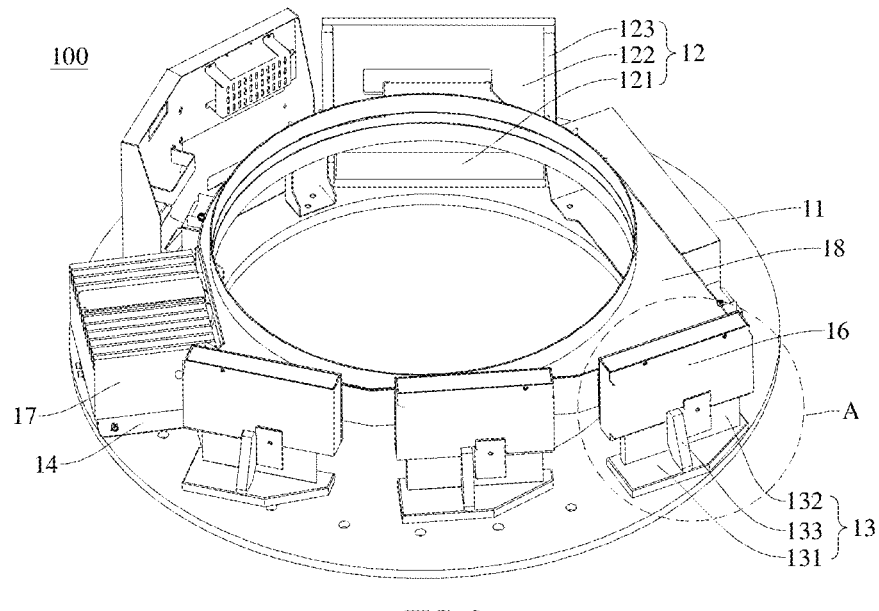
FIG. 3 is a three-dimensional view of the CT imaging system according to the embodiment shown in FIG. 1 in another orientation.

As shown in FIGS. 1 to 3, the CT imaging system 100 according to embodiments of the present disclosure includes: a connecting plate 11, a strong supporting frame, a weak supporting frame 14, an emitter 15, a detector 16, an electrical component 17, and a shielding box 18.

The connecting plate 11 is annular and has a rotating axis. The strong supporting frame is connected to the connecting plate 11 on a side of the connecting plate 11, and the strong supporting frame includes a first strong supporting frame 12 and a second strong supporting frame 13 distributed at an interval in a circumferential direction of the connecting plate 11. The weak supporting frame 14 is connected to the connecting plate 11 on a same side of the connecting plate 11 as the strong supporting frame.

It should be noted that, the structural strength of the strong supporting frame is higher than that of the weak supporting frame 14. Therefore, the weight of the strong supporting frame is also greater than that of the weak supporting frame 14.

The emitter 15 is connected to the first strong supporting frame 12. The detector 16 is connected to the second strong supporting frame 13. The electrical component 17 is connected to the weak supporting frame 14. The shielding box 18 is annular, an annular shielding cavity 180 with an opening facing the rotating axis is formed inside the shielding box 18, the shielding cavity 180 is provided with an inlet 181 at the emitter 15 and an outlet 182 at the detector 16, and the shielding box 18 is connected to at least one weak supporting frame 14.

It may be understood that the CT imaging system 100 receives through the detector 16 the ray generated by the emitter 15 to achieve CT imaging. A deviation generated in any of the detector 16 or the emitter 15 may cause errors in a ray signal received by the detector 16, affecting the definition of the CT image.

Therefore, the emitter 15 and the detector 16 are fixed on the connecting plate 11 through the strong supporting frame, which may ensure the connection strength between the emitter 15 and the connecting plate 11 as well as the connection strength between the detector 16 and the connecting plate 11, and reduce or avoid the deviation of the emitter 15 and the detector 16 relative to the connecting plate 11, thereby ensuring the definition of the CT image.

The deviation of the electrical component 17 and the shielding box 18 relative to the connecting plate 11 may not affect their own functions, nor may it affect CT imaging. Therefore, the connection strength requirement of the electrical component 17 and the shielding box 18 on the connecting plate 11 is lower than that of the emitter 15 and the detector 16.

Therefore, the electrical component 17 and the shielding box 18 are fixed on the connecting plate 11 through the weak supporting frame 14, which may meet the fixation requirements of the electrical component 17 and the shielding box 18. The light weight of the weak supporting frame 14 is conducive to the overall lightweight of CT imaging system 100, reducing the resistance of the CT imaging system 100 when rotating or moving, and improving the stability of operation of the CT imaging system 100.

In the CT imaging system 100 of the present disclosure, a stable connection between the emitter 15 and the connecting plate 11 as well as a stable connection between the detector 16 and the connecting plate 11 are ensured through the strong supporting frame, thereby ensuring the imaging effect of the CT imaging system 100, while a connection between the electrical component 17 and the connecting plate 11 as well as a connection between the shielding box 18 and the connecting plate 11 are achieved through the weak supporting frame 14, reducing the weight of the connection structure and facilitating the overall lightweight of the CT imaging system 100.

In some embodiments, as shown in FIGS. 1 to 3, the connecting plate 11 is provided with a plurality of mounting holes 111, and each of the strong supporting frame and the weak supporting frame 14 is fitted at the mounting hole 111 through a fastener. In such structure, each of the strong supporting frame and the weak supporting frame 14 has a plurality of fit locations on the connecting plate 11.

It may be understood that the strong supporting frame, the weak supporting frame 14, the emitter 15, the detector 16, the electrical component 17, and the shielding box 18 have different weights, and the weight distribution on the connecting plate 11 may affect the movement or rotation of the CT imaging system 100.

Therefore, the mounting locations of the emitter 15, the detector 16, the electrical component 17 and the shielding box 18 on the connecting plate 11 may be adjusted according to their own weights, so that the weight distribution on the connecting plate 11 is more uniform, thereby improving the stability of movement or rotation of the CT imaging system 100.

In addition, one strong supporting frame or weak supporting frame 14 may correspond to a plurality of mounting holes 111, thereby improving the stability of the strong supporting frame or the weak supporting frame 14 on the connecting plate 11.

In some embodiments, as shown in FIGS. 2 and 3, the first strong supporting frame 12 includes: a first flat supporting plate 121, a first upright plate 122, and two first ear plates 123.

The first flat supporting plate 121 is tightly attached to the connecting plate 11. The contact surface between the first flat supporting plate 121 and the connecting plate 11 is relatively large, so that the connecting plate 11 may provide a stable support to the first flat supporting plate 121, and the first flat supporting plate 121 is not easily deformed.

The first upright plate 122 is vertically provided on a side of the first flat supporting plate 121 away from the rotating axis, the first upright plate 122 is welded on the first flat supporting plate 121, and the first upright plate 122 is provided with a first opening directly facing the inlet.

Two first ear plates 123 are located at opposite ends of the first flat supporting plate 121, and each of the two first ear plates 123 is welded to the first upright plate 122 and the first flat supporting plate 121. In such structure, the first ear plate 123 provides a support to the first upright plate 122 in a radial direction of the connecting plate 11.

The emitter 15 is connected to the first upright plate 122, and the emitter 15 is located on a side of the first upright plate 122 away from the shielding box 18, so that the ray generated by the emitter 15 may penetrate the first upright plate 122 through the first opening.

In this way, the first flat supporting plate 121 provides a stable support to the first upright plate 122. Two first ear plates 123 are connected to both the first flat supporting plate 121 and the first upright plate 122, forming a triangular support structure at opposite ends of the first flat supporting plate 121, so that the first upright plate 122 has good load-bearing capacity in the radial direction of the connecting plate 11, which may reduce or avoid the shaking of the first upright plate 122. Therefore, the first upright plate 122 provides stable support force to the emitter 15 in the radial direction of the connecting plate 11, which may reduce or avoid the shaking of the emitter 15 and ensure the stability of the emitter 15 on the connecting plate 11, thereby improving the definition of the CT image.

Furthermore, the first upright plate 122 is provided with a plurality of connecting threaded holes 125, and the emitter 15 is fixed at the plurality of connecting threaded holes 125 through a threaded component, so that the first upright plate 122 may provide inward and outward support force to the emitter 15 in the radial direction of the connecting plate 11, ensuring a stable connection between the emitter 15 and the first upright plate 122.

While the strong supporting frame further includes a supporting auxiliary plate 124, and the emitter 15 is located between the supporting auxiliary plate 124 and the first upright plate 122, so that the supporting auxiliary plate 124 may provide inward support force to the emitter 15 in the radial direction of the connecting plate 11.

In this way, both the supporting auxiliary plate 124 and the first upright plate 122 provide a support to the emitter 15, so that the emitter 15 may be stably fixed on the connecting plate 11.

In some embodiments, as shown in FIGS. 1 to 3, at least two detectors 16 are arranged at intervals sequentially in the circumferential direction of the connecting plate 11, each of the at least two detectors 16 is connected to the second strong supporting frame 13, and the shielding box 18 is provided with the outlet 182 corresponding to each of the at least two detectors 16.

It may be understood that the shielding box 18 may block the ray, so as to prevent the ray from irradiating into the external environment of the CT imaging system 100. The outlet 182 is provided corresponding to the detector 16, so that the ray may enter the detector 16 through the outlet 182, which not only improves the safety of the CT imaging system 100, but also ensures that the detector 16 is less interfered with when receiving the ray.

In this way, a plurality of detectors 16 are provided to reduce the error of CT imaging. Each detector 16 is independently fixed on the connecting plate 11 through the second strong supporting frame 13, so that there is no connection relationship between the detectors 16, ensuring that the fixations of the detectors 16 do not affect each other, thereby improving the stability of the connection between each detector 16 and the connecting plate 11.

Figure 4:
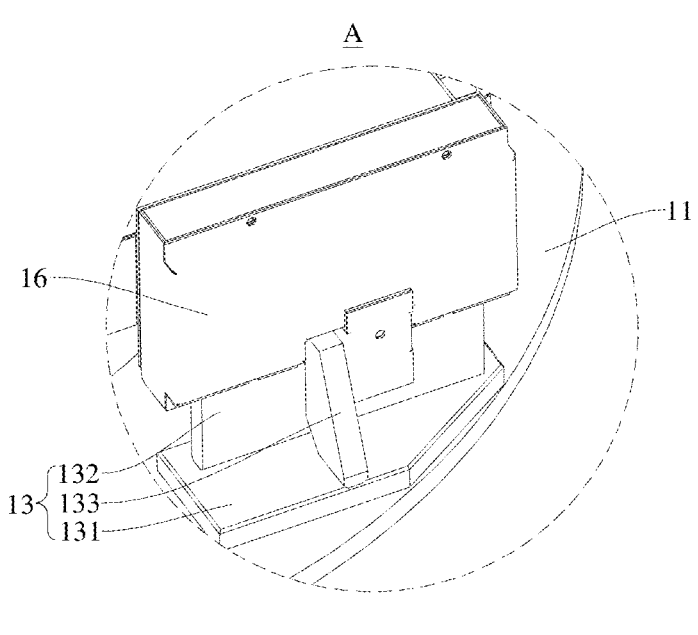
FIG. 4 is an enlarged structural diagram of a portion shown at a location A in FIG. 3.

Furthermore, as shown in FIG. 4, each second strong supporting frame 13 includes: a second flat supporting plate 131, a second upright plate 132, and a second ear plate 133.

The second flat supporting plate 131 is tightly attached to the connecting plate 11. The contact surface between the second flat supporting plate 131 and the connecting plate 11 is relatively large, so that the connecting plate 11 may provide a stable support to the second flat supporting plate 131, and the second flat supporting plate 131 is not easily deformed.

The second upright plate 132 is vertically provided and welded on the second flat supporting plate 131.

The second ear plate 133 is located on a side of the second upright plate 132 away from the shielding box 18, and the second ear plate 133 is welded to both the second flat supporting plate 131 and the second upright plate 132. In such structure, the second ear plate 133 provides a support to the second upright plate 132 in the radial direction of the connecting plate 11.

In this way, the second flat supporting plate 131 provides a stable support to the second upright plate 132. The second ear plate 133 is connected to both the second flat supporting plate 131 and the second upright plate 132, forming a triangular support structure between the second flat supporting plate 131 and the second upright plate 132, so that the second upright plate 132 has good load-bearing capacity in the radial direction of the connecting plate 11, which may reduce or avoid the shaking of the second upright plate 132. The detector 16 is connected to the second upright plate 132, and the second upright plate 132 provides the support force to the detector 16 in the radial direction of the connecting plate 11, which may reduce or avoid the shaking of the detector 16 and ensure the stability of the detector 16 on the connecting plate 11, thereby improving the definition of the CT image.

In some embodiments, the connecting plate 11 is a cast component, the strong supporting frame is a welded or cast component, and the weak supporting frame 14 is a sheet metal component.

It may be understood that the structure of each of the welded component and the cast component has a relatively large thickness, relatively high structural strength, and relatively large weight. In contrast, the sheet metal component usually has a relatively small thickness, so that it has relatively small weight, and its structural strength is lower than that of each of the welded component and the cast component.

Therefore, for the strong supporting frame and the weak supporting frame 14, the strong supporting frame has relatively high structural strength and relatively large mass, while the weak supporting frame 14 has relatively low structural strength and relatively small mass.

In addition, using the cast component as the connecting plate 11 may ensure the structural strength of the connecting plate 11, thereby ensuring the stability of the connection between the weak supporting frame 14 and the connecting plate 11 as well as the stability of the connection between the strong supporting frame and the connecting plate 11. Using the sheet metal component as the weak supporting frame 14 may reduce the assembly difficulty of the weak supporting frame 14 on the connecting plate 11, thereby reducing the mounting difficulty of the electrical component 17 and the shielding box 18 on the connecting plate 11. Using standardized cast components as the first strong supporting frame 12 and the second strong supporting frame 13 may reduce casting costs.

In some embodiments, as shown in FIG. 1, the shielding box 18 is a sheet metal component which has a smaller weight. The shielding box 18 is provided with a plurality of connecting ears 183, and the connecting ear 183 is connected to at least one of the weak supporting frame 14, the electrical component 17, or the strong supporting frame.

It may be understood that the ray is constrained inside the shielding box 18. The shielding box 18 has a relatively large volume to ensure the detection effect of the ray.

Therefore, the shielding box 18 is connected to the connecting plate 11 through a plurality of connecting ears 183, so that the shielding box 18 has a plurality of fixed locations, which may improve the stability of the connection between the shielding box 18 and the connecting plate 11. Due to the relatively large volume of the shielding box 18, the shielding box 18 is easy to be overlapped with the weak supporting frame 14, the electrical component 17, or the strong supporting frame. At this point, the weak supporting frame 14, the electrical component 17, and the strong supporting frame are all fixed on the connecting plate 11. The connection between the shielding box 18 and the connecting plate 11 may be achieved by directly connecting the connecting ear 183 to the weak supporting frame 14, the electrical component 17, or the strong supporting frame.

Furthermore, an inner perimeter wall of the shielding box 18 is circular, the connecting plate 11 is toroidal, and the inner perimeter wall of the shielding box 18 is coaxial with the connecting plate 11. An inner diameter of the shielding box 18 is less than an inner diameter of the connecting plate 11.

It may be understood that the annular interior of the connecting plate 11 is used to pass through the object to be detected. Therefore, the inner diameter of the shielding box 18 is set to be less than the inner diameter of the connecting plate 11, so that the shielding box 18 may block the gap between the object to be detected and the connecting plate 11, thereby improving the shielding effect of the shielding box 18 on the ray.

While the shape of the inner perimeter wall of the shielding box 18 corresponds to the inner perimeter of the connecting plate 11, so that the region surrounded by the inner perimeter wall of the shielding box 18 may have a relatively large space, and a larger object to be detected may pass through the shielding box 18.

Figure 5:
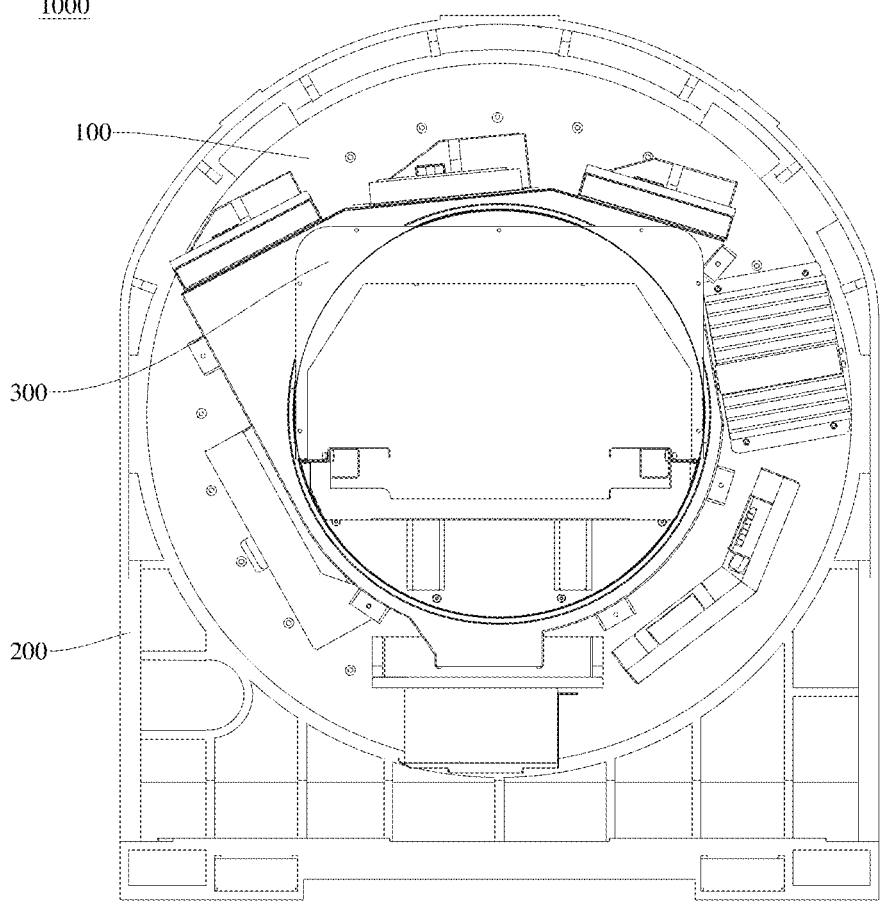
FIG. 5 is a schematic structural diagram of a CT detection device according to an embodiment of the present disclosure.

As shown in FIG. 5, the CT detection device 1000 according to embodiments of the present disclosure includes: a supporting framework 200, a slip ring bearing (not shown in the figure), the CT imaging system 100, and a detection channel 300.

The supporting framework 200 is provided with a bearing mounting hole. The slip ring bearing is arranged in the bearing mounting hole. The CT imaging system 100 is the CT imaging system 100 in above embodiments, where the connecting plate 11 is connected to the slip ring bearing so that the connecting plate 11 is rotatable relative to the supporting framework 200. The detection channel 300 is mounted on the supporting framework 200, where the detection channel 300 penetrates the shielding box 18.

It may be understood that the connecting plate 11 drives the CT imaging system 100 to rotate relative to the supporting frame 200, so that the CT imaging system 100 may perform CT imaging on the object to be detected at different angles. During the rotation process of the CT imaging system 100, the weight on the connecting plate 11 may affect the rotation of the CT imaging system 100.

In the CT detection device 1000 of the present disclosure, by using the CT imaging system 100 in above embodiments, some components in the CT imaging system 100 are connected by using the weak supporting frame 14, so that the overall lightweight of the CT imaging system 100 may be achieved while ensuring the imaging effect, thereby improving the stability of the CT imaging system 100 when the CT imaging system 100 rotates relative to the supporting framework 200, and improving the overall stability and detection effect of the CT detection device 1000.

The other components and operations of the CT imaging system 100 and the CT detection device 1000 according to embodiments of the present disclosure are known to those ordinary skilled in the art, which will not be described in detail here.

In the description of this specification, descriptions in reference of the terms "embodiment", "example", etc. refer to that the specific features, structures, materials, or characteristics described in conjunction with the embodiment or example are included in at least one embodiment or example of the present disclosure. In this specification, the illustrative expressions of the above terms may not necessarily refer to the same embodiment or example. Moreover, the specific features, structures, materials, or characteristics described may be combined in an appropriate manner in any one or more embodiments or examples.

Although embodiments of the present disclosure have been shown and described, those ordinary skilled in the art may understand that various changes, modifications, substitutions, and variations may be made to these embodiments without departing from the principles and purposes of the present disclosure, and the scope of the present disclosure is defined by the claims and their equivalents.

What is claimed is:

1. A CT imaging system, comprising:
a connecting plate being annular and having a rotating axis;
a strong supporting frame connected to the connecting plate on a side of the connecting plate, wherein the strong supporting frame comprises a first strong supporting frame and a second strong supporting frame distributed at an interval in a circumferential direction of the connecting plate;
a weak supporting frame connected to the connecting plate on a same side of the connecting plate as the strong supporting frame;
an emitter connected to the first strong supporting frame;
a detector connected to the second strong supporting frame;
an electrical component connected to the weak supporting frame; and
a shielding box being annular, wherein an annular shielding cavity with an opening facing the rotating axis is formed inside the shielding box, the shielding cavity is provided with an inlet at the emitter and an outlet at the detector, and the shielding box is connected to at least one weak supporting frame.

2. The CT imaging system according to claim 1, wherein the connecting plate is provided with a plurality of mounting holes, and each of the strong supporting frame and the weak supporting frame is fitted at the mounting hole through a fastener.

3. The CT imaging system according to claim 1, wherein the first strong supporting frame comprises:
a first flat supporting plate tightly attached to the connecting plate;
a first upright plate vertically provided on a side of the first flat supporting plate away from the rotating axis, wherein the first upright plate is welded on the first flat supporting plate, and the first upright plate is provided with a first opening directly facing the inlet; and
two first ear plates located at opposite ends of the first flat supporting plate, wherein each of the two first ear plates is welded to the first upright plate and the first flat supporting plate,
wherein the emitter is connected to the first upright plate, and the emitter is located on a side of the first upright plate away from the shielding box.

4. The CT imaging system according to claim 3, wherein the first upright plate is provided with a plurality of connecting threaded holes, and the emitter is fixed at the plurality of connecting threaded holes through a threaded component; and
wherein the strong supporting frame further comprises a supporting auxiliary plate, and the emitter is located between the supporting auxiliary plate and the first upright plate.

5. The CT imaging system according to claim 1, wherein at least two detectors are arranged at intervals sequentially in the circumferential direction of the connecting plate, each of the at least two detectors is connected to the second strong supporting frame, and the shielding box is provided with the outlet corresponding to each of the at least two detectors.

6. The CT imaging system according to claim 5, wherein each second strong supporting frame comprises:
a second flat supporting plate tightly attached to the connecting plate;
a second upright plate vertically provided and welded on the second flat supporting plate; and
a second ear plate located on a side of the second upright plate away from the shielding box, wherein the second ear plate is welded to the second flat supporting plate and the second upright plate,
wherein the detector is connected to the second upright plate.

7. The CT imaging system according to claim 1, wherein the connecting plate is a cast component, the strong supporting frame is a welded or cast component, and the weak supporting frame is a sheet metal component.

8. The CT imaging system according to claim 1, wherein the shielding box is a sheet metal component, the shielding box is provided with a plurality of connecting ears, and the connecting ear is connected to at least one of the weak supporting frame, the electrical component, or the strong supporting frame.

9. The CT imaging system according to claim 1, wherein an inner perimeter wall of the shielding box is circular, the connecting plate is toroidal, and the inner perimeter wall of the shielding box is coaxial with the connecting plate; and
wherein an inner diameter of the shielding box is less than an inner diameter of the connecting plate.

10. A CT detection device, comprising:
a supporting framework provided with a bearing mounting hole;
a slip ring bearing arranged in the bearing mounting hole;
a CT imaging system, wherein the CT imaging system is the CT imaging system according to claim 1, and the connecting plate is connected to the slip ring bearing so that the connecting plate is rotatable relative to the supporting framework; and
a detection channel mounted on the supporting framework, wherein the detection channel penetrates the shielding box.

* * * * *